United States Patent [19]
Brown et al.

[11] 3,962,266

[45] June 8, 1976

[54] NOVEL SUBSTITUTED BENZOPYRANOPYRIDINE

[75] Inventors: Richard E. Brown, East Hanover; Chester Puchalski, Dover; John Shavel, Jr., Mendham, all of N.J.

[73] Assignee: Warner-Lambert Company, Morris Plains, N.J.

[22] Filed: May 1, 1975

[21] Appl. No.: 573,668

Related U.S. Application Data

[63] Continuation-in-part of Ser. No. 534,502, Dec. 19, 1974, which is a continuation-in-part of Ser. No. 343,613, March 21, 1973, abandoned, which is a continuation-in-part of Ser. No. 122,498, March 9, 1971, abandoned.

[52] U.S. Cl. .............................. 260/295 T; 424/263
[51] Int. Cl.² ........................................ C07D 519/00

[58] Field of Search ................................ 260/295 T

[56] References Cited
UNITED STATES PATENTS

| | | |
|---|---|---|
| 3,396,165 | 8/1968 | Bolger .......................... 260/295.5 T |
| 3,429,889 | 2/1969 | Shulgin ............................. 260/295 T |
| 3,514,464 | 5/1970 | Pars et al. ........................ 260/295 T |
| 3,689,497 | 9/1972 | Brown et al. ..................... 260/295 T |
| 3,803,153 | 4/1974 | Villani .............................. 260/295 T |

*Primary Examiner*—Norman A. Drezin
*Attorney, Agent, or Firm*—Albert H. Graddis; Frank S. Chow; George M. Yahwak

[57] ABSTRACT

Disclosed is a novel substituted benzopyranopyridine which is active as a bronchodilator agent.

2 Claims, No Drawings

NOVEL SUBSTITUTED BENZOPYRANOPYRIDINE

This application is a continuation-in-part of application Ser. No. 534,502, filed Dec. 19, 1974, the disclosure of which is hereby incorporated by reference, which is in turn a continuation-in-part of our application Ser. No. 343,613, filed Mar. 21, 1973 and now abandoned, the disclosure of which is hereby incorporated by reference, which is in turn a continuation-in-part of our application Ser. No. 122,498, filed Mar. 9, 1971 and now abandoned.

This invention relates to novel substituted benzopyranopyridines of the formula I:

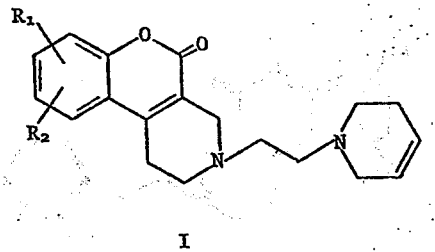

I

In the above formula, $R_1$ and $R_2$ may be hydrogen, hydroxy, lower alkoxy or lower alkyl of 1 to 6 carbon atoms or may be taken together to form a methylenedioxy group.

The compounds of this invention are prepared by reacting a substituted benzopyranopyridine of structure II with a suitable alkylating agent of structure III. In structure II, $R_1$ and $R_2$ are as defined for formula I. In structure III, hal. refers to halogen and may be chlorine, bromine or iodine.

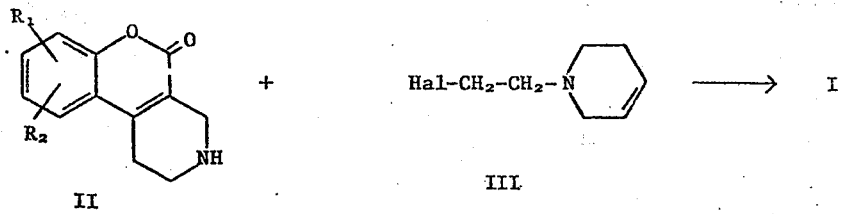

The starting materials according to structure II are described in our application Ser. No. 534,502. The alkylation reactions are carried out in a suitable solvent in the presence of a base to serve as proton acceptor.

Among the solvents which may be used are alcohols of 1 to 6 carbon atoms such as methanol, ethanol or amyl alcohol; polar aprotic solvents as dimethylformamide, dimethylsulfoxide and the like, tetrahydrofuran and dioxane. Suitable bases are potassium carbonate, sodium acetate or triethylamine and the like.

The alkylating agents according to structure III are known compounds and were prepared according to the procedure described (P. Chabrier, et al., *Bull. Soc. Chim. Fi.*, 1957, 1365).

The following examples are given in order to further illustrate the invention:

EXAMPLE 1

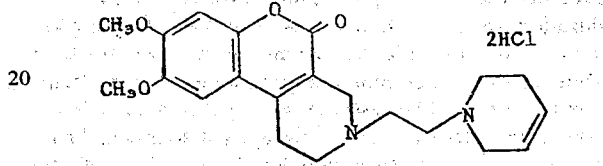

1,2,3,4-Tetrahydro-8,9-dimethoxy-3-[2-(1,2,3,6-tetrahydro-1-pyrioyl) ethyl]-5H-[1]benzopyrano[3,4-c]pyridin-5-one dihydrochloride. A mixture of 0.04m of 1,2,3,4-tetrahydro-8,9-dimethoxy-5H-[1]benzopyrano [3,4-c]pyridin-5-one, 0.047m of N-(2-chloroethyl)1,2,3,6-tetrahydropyridine HCl and 0.05m of triethylamine was refluxed for 6 hours, filtered while hot and treated immediately with excess HCl gas. The crude product was crystallized from methanol to give 7.8g of material, m.p. 236°–9° C.

Anal. Calcd. for $C_{21}H_{26}N_2O_4$ 2HCl: C, 56.89; H, 6.37; N, 6.32; Cl, 15.99. Found: C, 56.65; H, 6.30; N, 6.17; Cl, 15.83.

EXAMPLE 2

| | |
|---|---|
| TEST ANIMAL: | Male albino guinea pigs (250–350 gm) |
| ROUTE OF ADMINISTRATION: | Intraperitoneal |
| DOSES: | 25 mg/kg |
| SPASMOGENS: | Acetylcholine chloride 0.3% <br> Histamine 0.1% (most frequently <br> Methacholine chloride (Mecholyl) 0.1% used) <br> Serotonin creatinine sulfate 1.25% |
| PROCEDURE: | Pigs are continuously exposed to a spasmogen for 10 min.; delivery is by means of two 0 nebulizers (each nebulizer dispenses 0.2 cc/min.) positioned at the back of a closed, six unit plexiglas chamber (19 × 12½ × 9 in.) and driven by an air pressure of 10 lbs/in². The time from onset of the aerosol treatment to collapse of each animal is recorded; mean values for drug treated animals are compared to those of animals treated with vehicle. Guinea pigs that do not collapse during the 10 min. period are removed from the chamber and a maximum score of 10 is recorded. Test compounds (25 mg/kg, i.p.) are given 15 min. before exposure to spasmogen. |

(See Siegmund, O. H. et al.: J. Pharmacol and Exptl. Therapeutics, 90: 254, 1949)

Twelve animals were tested for bronchodilation according to Example II. Histamine was used as the spasmogen in all instances. Two separate tests were run with the results given in Table I:

TABLE I

| DOSE | No. ANIMALS | COLLAPSE TIME (MIN.) |
|---|---|---|
| control | 3 | 1.7 |
| 25 mg (Example 1) | 3 | 9.1 |
| control | 3 | 2.8 |
| 25 mg (Example 1) | 3 | 10.0 |

The protection which the compound of Example 1 has can be easily seen from this table.

The compound of Example 1 is active as a bronchodilator for all spasmogens listed in Example 2, and protects the guinea pig against bronchospasm for a duration up to four hours at an oral dose of 10 mg/kg. Thus, it is more effective against bronchospasm than aminophylline, a commercial product used in the treatment of bronchial asthma and pulmonary edema, which protects the guinea pig against identical bronchospasm for less than two hours at a dose of 100 mg/kg. In addition, the compound of Example 1 reverses pilocarpine or histamine bronchoconstriction in the dog for a duration of up to 1 hour at an oral dose of 10 mg/kg. The bronchodilator activity exhibited by the N-substituted benzopyrano[3,4-c] pyridine described in this invention is the result of a direct smooth muscle relaxant effect on the bronchial tree as shown by in vitro experiments on guinea pig trachea. In these experiments, the N-substituted benzopyrano [3,4-c]pyridine is approximately 75 times more active than aminophylline in relaxing tracheal smooth muscle.

The compounds of this invention are useful for the treatment of bronchial asthma. Generally speaking, a dose of about 500 mg to 1000 mg several times daily is recommended for mammals weighing about 70 kilograms. The compounds can be administered orally or by parenteral administration.

In order to use these compounds they are formulated with pharmaceutically acceptable excipients such as lactose, starch, powdered sugar and the dosage forms can be tablets, capsules and the like. The dosage regimen can be varied according to the condition being treated by methods well known to the healing arts.

We claim:

1. A substituted benzopyranopyridine of the formula;

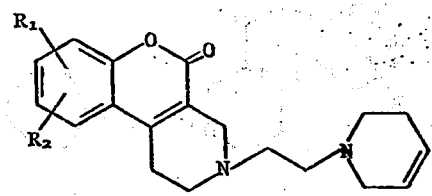

I wherein $R_1$ and $R_2$ may be hydrogen, hydroxy, lower alkoxy, or lower alkyl of 1 to 6 carbon atoms or taken together from a methylenedioxy group.

2. The compound according to claim 1 which is 1,2,3,4-tetrahydro-8,9-dimethoxy-3-[2-(1,2,3,6-tetrahydro-1-pyridyl)ethyl]-5H-[1]benzopyrano[3,4-c]pyridin-5-one.

* * * * *